US012758402B2

(12) United States Patent
Calvier

(10) Patent No.: US 12,758,402 B2
(45) Date of Patent: Oct. 13, 2026

(54) DEVICE AND METHOD FOR TAKING DIGITISATION IMPRESSIONS FOR GENERATING A 3D MODEL OF A FEMORAL PROSTHESIS SOCKET

(71) Applicant: VYTRUVE, Cesson Sevigne (FR)

(72) Inventor: Erwan Calvier, Cesson Sevigne (FR)

(73) Assignee: VYTRUVE, Cesson Sevigne (FR)

( * ) Notice: Subject to any disclaimer, the term of this patent is extended or adjusted under 35 U.S.C. 154(b) by 414 days.

(21) Appl. No.: 18/563,117

(22) PCT Filed: May 16, 2022

(86) PCT No.: PCT/EP2022/063208
§ 371 (c)(1),
(2) Date: Dec. 7, 2023

(87) PCT Pub. No.: WO2022/243255
PCT Pub. Date: Nov. 24, 2022

(65) Prior Publication Data

US 2024/0261116 A1 Aug. 8, 2024

(30) Foreign Application Priority Data

May 21, 2021 (FR) ...................................... 2105336

(51) Int. Cl.
*A61B 5/00* (2006.01)
*A61B 5/107* (2006.01)
(Continued)

(52) U.S. Cl.
CPC .......... *A61F 2/5046* (2013.01); *A61B 5/1077* (2013.01); *A61B 5/702* (2013.01); *A61F 2002/505* (2013.01)

(58) Field of Classification Search
None
See application file for complete search history.

(56) References Cited

U.S. PATENT DOCUMENTS 4,988,360 A * 1/1991 Shamp ...................... A61F 2/80 623/36
5,258,037 A * 11/1993 Caspers .................... A61F 2/72 623/36
(Continued)

FOREIGN PATENT DOCUMENTS

WO WO-2010006728 A1 * 1/2010 ............. G06T 19/20
WO WO-2013142343 A1 * 9/2013 ............... A61F 2/80

OTHER PUBLICATIONS

Aug. 22, 2022 International Search Report issued in International Patent Application No. PCT/EP2022/063208.
(Continued)

*Primary Examiner* — Ann Hu
(74) *Attorney, Agent, or Firm* — Williams Mullen; R. Brian Drozd

(57) ABSTRACT

A device for assisting taking digitisation impressions of the remaining part of an amputated limb of a patient for generating a 3D model of a femoral prosthesis socket, that includes: a base, at least two transparent tongues secured to the base and suitable for being applied against the remaining part of the amputated limb, and means for clamping said tongues on the remaining part of the amputated limb.

2 Claims, 4 Drawing Sheets

(51) Int. Cl.

| | |
|---|---|
| ***A61F 2/50*** | (2006.01) |
| ***A61F 2/76*** | (2006.01) |
| ***A61F 2/78*** | (2006.01) |
| ***A61F 2/80*** | (2006.01) |
| ***A61M 21/00*** | (2006.01) |

(56) References Cited

U.S. PATENT DOCUMENTS

| | | | | |
|---|---|---|---|---|
| 8,323,353 | B1 * | 12/2012 | Alley | A61F 2/80 623/33 |
| 8,423,167 | B2 * | 4/2013 | Sanders | A61F 2/5046 700/118 |
| 8,591,599 | B1 * | 11/2013 | Kaliki | A61F 2/78 623/36 |
| 8,978,224 | B2 * | 3/2015 | Hurley | A61F 2/54 29/407.1 |
| 9,050,202 | B2 * | 6/2015 | Bache | A61F 2/80 |
| 9,248,033 | B2 * | 2/2016 | Bache | A61F 2/80 |
| 9,468,542 | B2 * | 10/2016 | Hurley | A61F 2/80 |
| 9,636,238 | B2 * | 5/2017 | Sanders | A61F 2/76 |
| 9,962,273 | B2 * | 5/2018 | Bache | A61F 2/78 |
| 9,980,779 | B2 * | 5/2018 | Hurley | A61F 2/76 |
| 10,172,728 | B2 * | 1/2019 | Hurley | A61F 2/78 |
| 10,179,056 | B2 * | 1/2019 | Hurley | A61F 2/80 |
| 10,806,607 | B2 * | 10/2020 | Steinberg | A61F 2/80 |
| 2010/0115757 | A1 * | 5/2010 | Sacherer | A61F 2/5046 29/458 |
| 2014/0163697 | A1 * | 6/2014 | Sanders | A61F 2/5046 623/36 |
| 2015/0265434 | A1 * | 9/2015 | Hurley | A61F 2/5044 623/33 |
| 2016/0058584 | A1 * | 3/2016 | Cespedes | A61F 2/78 700/98 |
| 2018/0020973 | A1 * | 1/2018 | Hurley | A61F 2/76 623/24 |
| 2020/0390568 | A1 * | 12/2020 | Joseph | A61F 2/80 |

OTHER PUBLICATIONS

Aug. 22, 2022 Written Opinion issued in International Patent Application No. PCT/EP2022/063208.

* cited by examiner

[Fig. 1]
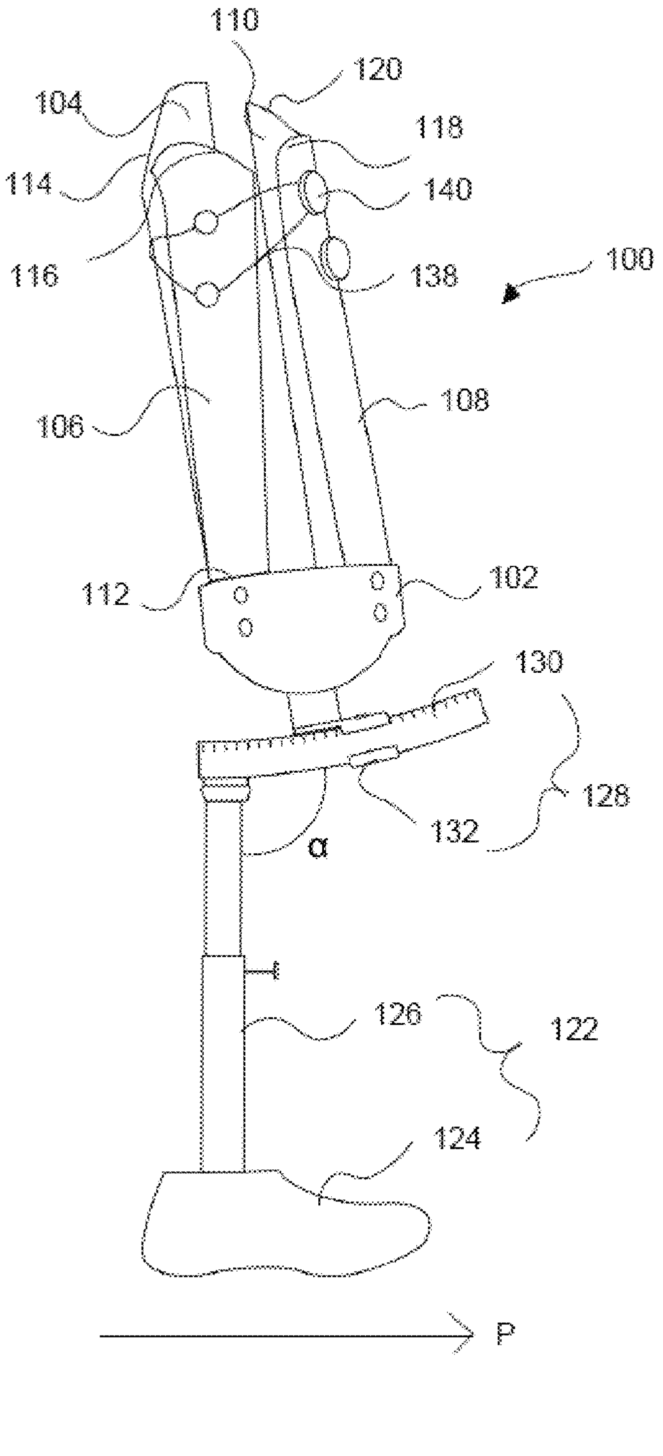

[Fig. 2]
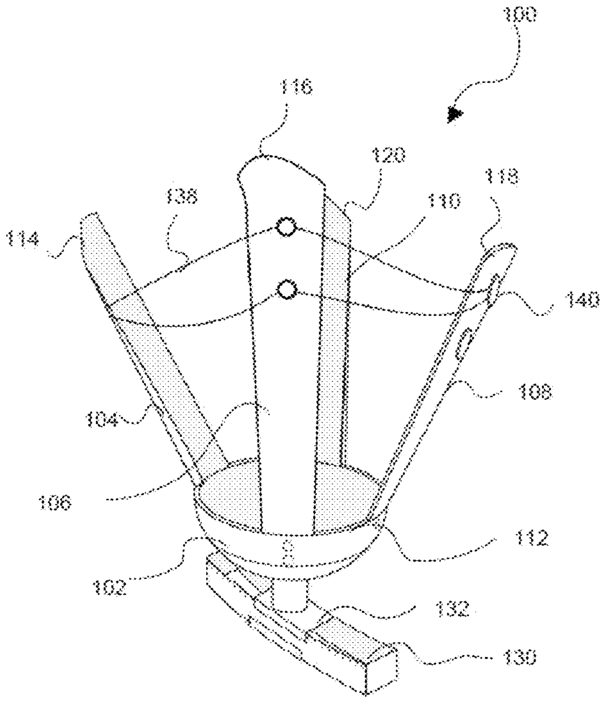

[Fig. 3]
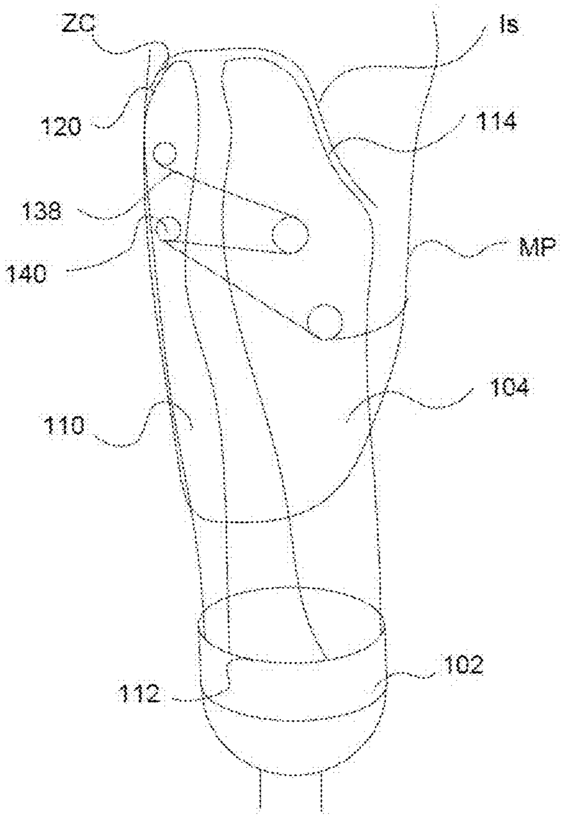

[Fig. 4]
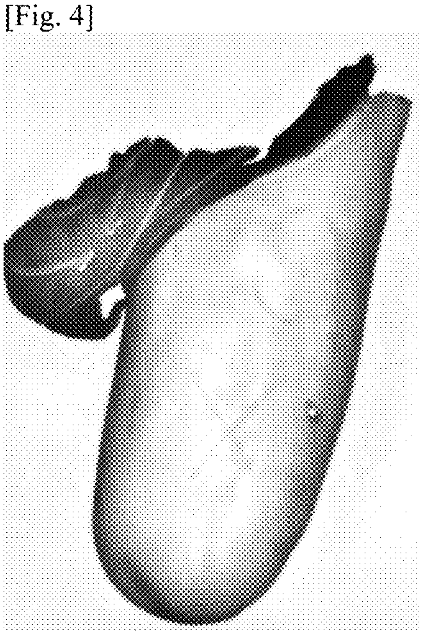
[Fig. 5]
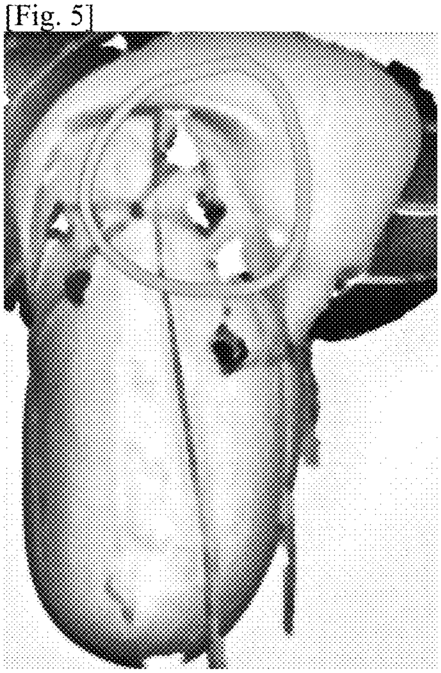

DEVICE AND METHOD FOR TAKING DIGITISATION IMPRESSIONS FOR GENERATING A 3D MODEL OF A FEMORAL PROSTHESIS SOCKET

The present invention relates to a device for assisting taking digitisation impressions of the remaining part of an amputated limb of the patient for generating a 3D model of a femoral prosthesis socket, with a view to the computer aided design of the femoral prosthesis.

The method for manufacturing prostheses for limbs after transfemoral amputation comprises several steps, including a step of taking impressions including determining the shape of the amputated limb, the location of important anatomical points such as the position of bone prominences, in particular of the ischium, and the necessary compression of the soft tissues. The traditional method consists in making a moulding of the remaining part of the amputated limb by means of plaster strips and manually locating and marking on the plaster the important anatomical parts.

This method is lengthy and tedious, needs a certain know-how and sometimes requires the presence of several prosthetists.

The aim of the present invention is to propose a sure, effective and reproducible method for taking digitisation impressions and designing a 3D model of a femoral prosthesis socket with a view to the computer aided design thereof, as well as a device for implementing said method.

For this purpose, the invention relates to a method for generating a 3D model of a femoral prosthesis socket for a patient with a view to computer aided design thereof, the method comprising a step of taking digitisation impressions comprising the following steps:

- marking at least one reference point on the remaining part of an amputated limb,
- 3D digitisation of the remaining part of the amputated limb by means of a scanner and obtaining a first digital model,
- installing, on the remaining part of the amputated limb, a device comprising a base, at least two transparent tongues secured to the base and means for clamping the tongues on the remaining part of the amputated limb,
- positioning said device by positioning the top edge of one of the tongues at the anterior edge of the ischium and obtaining the position of the ischium,
- clamping the clamping means to compress the soft tissues of the remaining part of the amputated limb with the tongues, and obtaining compression regions of the soft tissues,
- 3D digitisation of the remaining part of the amputated limb fitted with the device and obtaining a second digital model,
- superimposing the first and second 3D digital models obtained by aligning the reference points of each digital model,
- keeping on the second 3D digital model the top part on which the anterior edge of the ischium and the compression regions of the soft tissues are visible, eliminating the remaining bottom part and obtaining a truncated second 3D digital model,
- keeping on the first 3D digital model the bottom part allowing reconstitution, from the truncated second 3D digital model, of a complete 3D digital model, and eliminating the remaining part,
- generating a 3D model.

The method according to the invention makes it possible to obtain, digitally, the data or impressions necessary for generating a 3D model of a femoral prosthesis socket, these data or impressions including:

- the position of the ischium of the patient, and
- the compression of the soft tissues.

Thus the first and second steps consist in proceeding with markings, on the amputated limb, and then obtaining a first digital model on which the contour of the limb and the markings are visible. These markings will make it possible to superimpose the first and second 3D digital models obtained subsequently.

The third and fourth steps consist in installing the device according to the invention on the amputated limb. To do this, the device according to the invention is installed on the limb so that one of the transparent tongues is applied against the posterior face of the limb, below the ischium. More specifically, the top edge that the tongue has is applied just below the anterior edge of the ischium. The ischium is thus in abutment against this tongue when the patient is standing. The second tongue for its part can be applied for example against the exterior or interior face of the limb.

Once the device is put in place and the tongues positioned, the latter are clamped against the limb to compress the soft tissues, in a clamping intensity adapted to each patient. The compression exerted at the edges that the tongues have makes it possible to obtain compression regions.

In the subsequent step, a second 3D digital model is obtained, including the position of the ischium and the compression regions of the soft tissues.

The first and second 3D digital models are next superimposed by taking as the reference point, for this alignment, the markings made during the first step, these being visible on all the 3D digital models.

The first 3D digital model contains the shape of the amputated limb. The second 3D digital model contains the position of the ischium and the regions determining the compression of the soft tissues. An appropriate processing is then proceeded with so as to reconstitute, from the two 3D digital models, a 3D digital model allowing the computer aided design of a femoral prosthesis socket.

According to one embodiment of the invention, the method also comprises a step of adjusting the flexum of the hip of said patient, the device comprising to do this a floor support and means for adjusting the relative positions of said tongues secured to the base with respect to said floor support, as well as the anteroposterior angle formed between them.

During the step, the prosthetist positions the patient standing on the floor and proceeds with the adjustments of the device, using adjustment means provided for this purpose, respecting the natural angulation of his hip flexum so that the patient is bearing on the floor in a stable manner.

The invention also relates to a device for assisting taking digitisation impressions of the remaining part of an amputated limb of a patient for generating a 3D model of a femoral prosthesis socket, the device being characterised in that it comprises:

- a base,
- at least two transparent tongues secured to the base and suitable for being applied against the remaining part of the amputated limb,
- means for clamping the tongues on the remaining part of the amputated limb.

According to a preferred embodiment of the invention, the device also comprises:

- a floor support,
- a means for connection between said floor support and said base.

Advantageously, the connection means comprises means for adjusting the relative positions of said tongues secured to the base with respect to said floor support and the anteroposterior angle formed between them.

Preferentially, said adjustment means comprise a concave runner the concavity of which is turned towards the base and a guide that the base has, said guide being able to slide along said runner.

Advantageously, said floor support comprises a pedestal and a mast adjustable for height.

Preferentially, said pedestal is in the shape of a human foot.

Preferentially again, said floor support also comprises an articulated connection, preferentially a pivot.

According to one feature of the invention, the first of the tongues has a top edge that splays in the direction of the exterior.

According to another feature of the invention, the first tongue projects from a first portion of the top edge that the base has, the second tongue projects from a second portion of the top edge adjacent to the first portion.

Advantageously, the device comprises a third tongue that projects from a third portion of the top edge, preferentially facing the second portion.

Advantageously again, the device comprises a fourth tongue that projects from a fourth portion of the top edge, preferentially facing the first portion.

Preferentially, the means for clamping the tongues are in the form of one or more links extending between attachment means distributed on said tongues, said attachment means comprising means for winding said links.

FIG. 1 is a profile view of a device according to the invention,

FIG. 2 is a view of a part of a device according to the invention, installed on the remaining part of an amputated limb of a patient, FIG. 3 is a view of a part of a device according to the invention, installed on the remaining part of an amputated limb of a patient, FIG. 4 is an image of a first 3D digital model obtained in the method according to the invention, FIG. 5 is an image of a second 3D digital model obtained in the method according to the invention.

FIGS. 1 and 2 show a device 100 according to the invention for assisting taking digitisation impressions of the remaining part of an amputated limb of a patient for generating a 3D model of a femoral prosthesis socket.

On FIG. 3, the device 100 illustrated in FIG. 1 is installed on the remaining part of the amputated limb of a patient with a view to being scanned by the 3D scanner. Hereinafter, the "remaining part of the amputated limb" will be referred to as "limb". The device 100 comprises a base 102 and tongues 104, 106, 108, 110, secured to the base 102, made from transparent material.

The base 102 serves as a support for the tongues and here takes the form of a cup. It has a circular top edge 112.

The first tongue 104 projects from the base 102 from a first portion of the circular top edge 112 that corresponds to a first quarter of this edge. This first tongue is intended to be applied against the part of the limb of the patient that contains the ischium and is used to locate the position of the ischium. It has at its free end a top edge 114 inclined in the direction of the base 102 and intended to be applied against the anterior edge of the ischium. So as to optimise its application against the limb, the internal face of the tongue 104 is substantially concave.

The second tongue 106 projects from the quarter adjacent to the first quarter of the top edge 112 of the base 102. It is intended to be applied against the rear portion of the crotch and has a top edge 116 that splays in the direction of the exterior so as to hug the top of the crotch. So as to optimise its application against the limb, the internal face of the tongue 106 is also substantially concave.

The third tongue 108 projects from the quarter facing the first quarter of the top edge 112 of the base 102. It is intended to be applied against a front portion of the crotch and has a top edge 118 inclined in the direction of the base and substantially conforming to the fold of the groin. So as to optimise its application against the limb, the internal face of the tongue 108 is also substantially concave.

The fourth tongue 110 projects from the other quarter adjacent to the first quarter of the top edge 112 of the base 102. It is intended to be applied against the external face of the limb, the face including the greater trochanter, and has a top edge 120 inclined in the direction of the base 102. So as to optimise its application against the limb, the internal face of the tongue 110 is also substantially concave.

It should be noted that the determination of the respective shapes of the tongues can easily be assessed by a person skilled in the art, who is here a prosthetist and will be able to adapt these shapes to the regions of the limb against which they are applied. Moreover, devices 100 will be able to be designed without difficulty, some for right limbs, the others for left limbs.

So that the takings of impressions are more precise and best reproduce the conditions under which the limb will be fitted with the socket of its future prosthesis, the device 100 comprises a floor support 122 to place the patient in a standing position once the device 100 is installed on the limb.

The floor support 122 is composed of a pedestal 124, which is advantageously in the shape of a human foot, and a tubular mast 126 adjustable for height. Configuring the pedestal as a human foot and adjusting the height of the tubular mast 126 makes it possible to position the patient in a stable standing position when the impressions are taken. In particular, adjusting the mast 126 for height makes the device 100 usable with any patient.

The floor support 122 is connected to the base 102 by means of a connection means 128. To respect the flexum of the hip of the patient in a stable standing position, this connection means 128 allows this adjustment of the flexum and, to do this, comprises means for adjusting the relative positions of the tongues 104, 106, 108, 110 secured to the base 102 with respect to the floor support 122, and of the anteroposterior angle formed between them. The adjustment means comprise a concave runner 130, the concavity of which is turned towards the base 102, and a guide 132 that the base 102 has. The guide 132 can slide along the runner 130 in the anteroposterior direction P. To facilitate the use of the device 100 once fitted on the limb and in particular to enable the patient to sit if required, an articulated connection 134, such as a pivot, can furthermore be provided on the tubular mast 126, preferentially in proximity to the connection means 128 (FIG. 2).

The device 100 also comprises means for clamping the tongues 104, 106, 108, 110 against the limb. They are in the form of links 138 extending between attachment means 140 distributed on the tongues. The attachment means comprise means for winding the links 138 to provide clamping.

The device 100 is therefore used for taking digitisation impressions in a method for generating a 3D model of a femoral prosthesis socket for a patient with a view to computer aided design thereof. The steps of the method according to the invention are detailed hereinafter.

In a first step, prior to the placing of the device 100 on the limb, reference points are made thereon, such as dots or crosses, for example using a marker. In a second step, the limb is digitised by means of a suitable apparatus. A first 3D digital model is thus obtained, on which the contours of the limb are visible.

At the following step, the device 100 is installed on the limb MP (FIG. 3). Placing the device 100 on the limb MP, as illustrated on FIG. 3, is extremely simple and quick. The patient is positioned in a standing position and the limb MP is received in the space delimited by the tongues 104, 106, 108, 110. The top edge 114 of the first tongue 104 is applied against the anterior edge of the ischium. The second and third tongues 106 and 108 are applied respectively against the rear and front portions of the crotch region of the limb MP. The top edge 116 of the second tongue 106 is disposed at the top of the crotch. The top edge 118 of the third tongue is applied against the fold of the groin.

Once installed, the tongues are clamped against the limb MP by means of the clamping means 136, so as to compress the soft tissues.

The stability and the flexum of the hip of the patient are adjusted by sliding the runner 130 on the guide 132.

Once the clamping and the other adjustments have been implemented, the compression regions ZC of the soft tissues and the position of the ischium Is are visible on the limb MP (FIG. 3). At the following step, the limb thus fitted with the device 100 is digitised and a second 3D digital model is thus obtained, on which the compression regions of the soft tissues, the position of the ischium and the reference points produced on the limb are visible.

At the following step, the first and second 3D digital models obtained are superimposed by aligning the reference points of each 3D digital model.

On the second 3D digital model, only the top part on which the anterior edge of the ischium and the compression regions of the soft tissues are visible is kept. This corresponds approximately to the first ten centimetres, starting from the top of the model. The remaining bottom part is eliminated. A truncated second 3D digital model is then obtained.

On the first 3D digital model, only the bottom part necessary for reconstitution, from the second truncated 3D digital model, of a complete 3D digital model, is kept. The remaining part is eliminated.

The 3D model thus generated is able to be used for the computer aided design.

The invention claimed is:

1. A method for generating a 3D model of a femoral prosthesis socket for a patient with a view to computer aided design thereof, the method comprising a step of taking digitisation impressions comprising the following steps:

marking at least one reference point on the remaining part of an amputated limb, 3D digitisation of the remaining part of the amputated limb by means of a scanner and obtaining a first 3D digital model, installing, on the remaining part of the amputated limb, a device comprising a base, at least two transparent tongues secured to the base and means for clamping the tongues on the remaining part of the amputated limb, positioning said device by positioning a top edge of one of the tongues at the anterior edge of the ischium and obtaining the position of the ischium (Is), clamping the means for clamping to compress the soft tissues of the remaining part of the amputated limb with the tongues, and obtaining compression regions of the soft tissues, 3D digitisation of the remaining part of the amputated limb fitted with the device and obtaining a second 3D digital model, superimposing the first and second 3D digital models obtained by aligning the reference points of each 3D digital model, keeping on the top part of the second 3D digital model on which the anterior edge of the ischium and the compression regions of the soft tissues are visible, eliminating the remaining bottom part of the second 3D digital model and obtaining a truncated second 3D digital model, keeping on the bottom part of the first 3D digital model to allow reconstitution of the amputated limb, and eliminating the top part of the first 3D digital model, generating a complete 3D digital model based on the bottom part of the first 3D digital model and the top part of the second 3D digital model.

2. The method according to claim 1, wherein said device comprising in addition a floor support and means for adjusting the relative positions of said tongues, secured to the base, with respect to said floor support and the anteroposterior angle formed between them, the method comprises:

a step of adjusting the flexum of the hip of said patient.

* * * * *